United States Patent [19]

Schaeffer

[11] Patent Number: 5,102,665
[45] Date of Patent: Apr. 7, 1992

[54] PHARMACEUTICAL COMPOSITIONS

[75] Inventor: Alain E. E. Schaeffer, Saint Sébastien de Morsent, France

[73] Assignee: Glaxo Group Limited, London, England

[21] Appl. No.: 666,102

[22] Filed: Mar. 7, 1991

Related U.S. Application Data

[63] Continuation of Ser. No. 370,904, Jun. 23, 1989, abandoned.

[30] Foreign Application Priority Data

Jun. 24, 1988 [FR] France ................ 88 08497

[51] Int. Cl.$^5$ ................................ A61K 9/46
[52] U.S. Cl. ...................... 424/466; 424/446
[58] Field of Search .................. 424/446, 466

[56] References Cited

U.S. PATENT DOCUMENTS 4,824,664  4/1989  Tarral et al. .................. 424/446

FOREIGN PATENT DOCUMENTS

| 760288 | 12/1970 | Belgium . |
| 233853 | 8/1987 | European Pat. Off. . |
| 0396335 | 11/1990 | European Pat. Off. . |
| 2547727 | 12/1984 | France . |
| 1274797 | 5/1972 | United Kingdom . |
| 2142820 | 1/1985 | United Kingdom . |

Primary Examiner—Thurman K. Page
Assistant Examiner—William E. Benston, Jr.
Attorney, Agent, or Firm—Bacon & Thomas

[57] ABSTRACT

An effervescent pharmaceutical composition for oral use comprising ranitidine or a physiologically acceptable salt thereof, a monoalkali metal citrate, and an alkaline carbonate or bicarbonate.

33 Claims, No Drawings

PHARMACEUTICAL COMPOSITIONS

This application is a continuation of Ser. No. 07/370,904, Jun. 23, 1989, now abandoned.

The present invention relates to a pharmaceutical composition containing as active ingredient the histamine $H_2$-antagonist ranitidine, particularly a composition for oral administration.

Ranitidine, N-[2-[[[5-(dimethylamino)methyl-2-furanyl]methyl]thio]ethyl]-N'-methyl-2-nitro-1,1-ethenediamine, and its physiologically acceptable salts are described and claimed in French Patent Specification No. 7724021, and a particular crystalline form of ranitidine hydrochloride is described and claimed in French Patent Specification No. 8118528. In both these specifications there is reference to formulations for oral administration, which may take the form of for example tablets, capsules, granules, powders, solutions, syrups, suspensions, or tablets or lozenges for buccal administration. Oral preparations of ranitidine are also disclosed in French Patent Specification No. 8407305.

Ranitidine is a potent histamine $H_2$-antagonist which, in the form of its hydrochloride salt, is widely used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

Oral administration constitutes a preferred route for administering ranitidine, and effervescent compositions provide a useful and advantageous type of formulation for oral use. Prior to being taken by the patient, an effervescent composition is dissolved and/or dispersed in for example an aqueous medium, such as drinking water. Dissolution and/or dispersion takes place rapidly, with effervescence to give an agreeable presentation of the drug, particularly for patients who do not prefer to take tablets, or find difficulty in swallowing them. In addition, the solution or dispersion of the effervescent composition affords a liquid preparation containing a fixed dose of the drug, without any need for the patient to measure a prescribed volume.

Effervescent compositions usually contain, in addition to the active ingredient, a source of carbon dioxide (such as an alkaline carbonate or bicarbonate) and an acid (such as citric acid). According to published European Patent Specification No. 233853, however, the use of citric acid in effervescent compositions in which the active ingredient is a histamine $H_2$-antagonist presents a problem due to the instability of the $H_2$-antagonist in the presence of acid. Replacement of citric acid by monosodium citrate still fails to give a satisfactory level of stability, whilst replacement of the citric acid by disodium citrate results in insufficient effervescence and a prolonged dissolution time. Thus in order to maintain an acceptable level of effervescence without affecting the stability of the active ingredient, it is necessary, according to published European Patent Specification No. 233853, to replace the citric acid with a mixture of mono- and di-alkaline citrate, more particularly a mixture of monosodium or monopotassium citrate, and disodium or dipotassium citrate.

Although published European Patent Specification No. 233853 discloses effervescent compositions containing histamine $H_2$-antagonists in general, the only $H_2$-antagonist referred to specifically is cimetidine. More particularly, the specification contains no specific reference to effervescent compositions in which the active ingredient is ranitidine.

Contrary to the teaching of published European Patent Specification No. 233853, we have now found, surprisingly, that the $H_2$-antagonist ranitidine may be satisfactorily formulated as an effervescent composition, having the required degree of stability and a sufficiently rapid rate of dissolution, using a monoalkali metal citrate (more particularly monosodium citrate) alone. Furthermore, such effervescent compositions containing a monoalkali metal citrate alone are easier to manufacture than those containing a mixture of mono- and di-alkaline citrate.

Thus the present invention provides an effervescent pharmaceutical composition for oral use comprising ranitidine or a physiologically acceptable salt thereof, an alkali metal citrate, and an alkaline carbonate or bicarbonate, characterised in that the alkali metal citrate is solely a monoalkali metal citrate.

The monoalkali metal citrate may be for example monopotassium citrate or, more preferably, monosodium citrate.

The alkaline carbonate or bicarbonate may be for example an alkali metal (e.g. sodium or potassium) or an alkaline earth metal (e.g. magnesium or calcium) carbonate or bicarbonate, more preferably sodium bicarbonate.

It is preferred that ranitidine should be employed in the composition according to the invention in the form of a physiologically acceptable salt. Such salts include salts of inorganic or organic acids such as hydrochloride, hydrobromide, sulphate, acetate, maleate, succinate, fumarate and ascorbate salts. Ranitidine in the form of a hydrochloride salt is particularly preferred.

The amount of ranitidine, preferably in the form a physiologically acceptable salt, employed in the effervescent composition of the invention may be for example 50–600 mg, and will preferably be in the range of 50–500 mg, more preferably 150–300 mg, per dosage unit, expressed as the weight of free base. The ranitidine content of the effervescent composition (in the form of either free base or a physiologically acceptable salt) may be, for example, in the range of 2% to 30% on a weight-to-weight (w/w) basis.

The monoalkali metal citrate and alkaline carbonate or bicarbonate may each independently constitute, for example 25% to 55% (w/w), more preferably 35% to 45% (w/w), of the effervescent composition. The ratio of monoalkali metal citrate to alkaline carbonate or bicarbonate may conveniently be within the range of 1:2 to 2:1, more preferably 1:1.

A preferred effervescent composition according to the invention comprises ranitidine hydrochloride, monosodium citrate and sodium bicarbonate. More particularly, these three ingredients may be present in amounts of 2% to 30% (w/w), 25% to 55% (w/w) and 25% to 55% (w/w) respectively.

The effervescent compositions according to the invention are particularly intended for use in human medicine.

The composition may be administered, for example, 1 to 4 times per day, preferably once or twice. It will be appreciated that it may be necessary to make routine variations to the dosage depending on the age and weight of the patient.

The compositions may take the form of, for example, tablets, granules or powders, granules and powders conveniently being presented as a fixed dose in a sachet.

The effervescent compositions according to the invention may be formulated using additional physiologically acceptable carriers or excipients as appropriate. Such additional carriers or excipients are preferably water soluble or substantially water soluble, and may be for example binding agents such as polyvinylpyrrolidone and/or lubricants such as siliconed sodium benzoate or polyalkylene glycols. Dye(s) may also be included.

When the effervescent composition is formulated as tablets, these preferably contain 1% to 2% (w/w) of a binding agent (e.g. polyvinylpyrrolidone) and 2% to 4% (w/w) of a lubricant (e.g. siliconed sodium benzoate). When the effervescent composition is presented in a sachet, the product preferably contains 2% to 4% (w/w) of a binding agent (e.g. polyvinylpyrrolidone).

Since the effervescent composition is dissolved or dispersed prior to being taken by the patient, tablets in particular may be larger than conventional tablets, and this permits the inclusion of other ingredients such as a suitable antacid e.g. aluminium hydroxide or magnesium hydroxide.

The composition may also contain flavouring and/or sweetening agents, which serve to mask the inherently bitter taste associated with ranitidine. Suitable flavouring agents may be for example lemon, orange, grapefruit or mint. The sweetening agents may be for example intense sweeteners (e.g. sodium saccharin, sodium cyclamate, aspartame, thaumatin or acesulfam K). Mixtures of sweetening and/or flavouring agents may also be used. The precise amount of sweetening and/or flavouring agent(s) will depend upon the nature of the agent(s) being used, but will be sufficient to mask the bitter taste associated with ranitidine.

It is important that a formulation which is to be marketed should possess the required degree of stability. Effervescent compositions according to the invention have an adequate level of stability not only in the solid form, but also in the medium in which they are dispersed or dissolved by the patient.

The effervescent compositions according to the invention may be prepared according to conventional techniques well known in the pharmaceutical industry for the manufacture of tablets, granules and powders. Such methods are very simple to operate, and can readily be reproduced on a manufacturing scale. They are also easy to control, and use starting materials which are readily available. This is in contrast to the preparation of effervescent compositions according to European Patent Specification No. 233853 where, before addition of the histamine $H_2$-antagonist, it is necessary to prepare an effervescent 'couple' by mixing stoichiometric quantities of citric acid and an alkaline carbonate or bicarbonate, and allowing these to react until the precise point is reached where monoalkaline citrate and dialkaline citrate are present in the desired ratio.

For the preparation of effervescent compositions according to the invention, the ranitidine or ranitidine salt, monoalkali metal citrate, and alkaline carbonate or bicarbonate may, for example, be blended with suitable excipients and, if desired, granulated. If the manufacturing process includes granulation, this should preceed the addition of any flavouring agent(s). Any sweetening agent(s) may be added either before or after granulation. Tablets may be prepared, for example, by compression of the powder blend or granulate, using a lubricant as an aid to tabletting.

Since one of the characteristics of the compositions according to the invention is that they dissolve and/or disperse in water, it is important that the products should be manufactured, packed and stored under conditions of low moisture. Thus, for example, tablets may be packed individually in sealed strips made of a water-impervious material such as aluminium foil, or presented in suitable multidose containers (made of for example polypropylene) incorporating a dessicant (e.g. silica gel). Powders or granules may for example be presented in sealed water-impervious sachets, conveniently containing a single fixed dose.

The following examples illustrate effervescent compositions according to the invention, in which the active ingredient is ranitidine hydrochloride. Ranitidine free base or other physiologically acceptable salts thereof may be formulated in a similar manner.

Examples 1 to 5 illustrate effervescent tablets according to the invention.

EXAMPLE 1

|  | mg/2 g tablet |
| --- | --- |
| Ranitidine hydrochloride | 168.0* |
| Anhydrous monosodium citrate | 840.0 |
| Sodium bicarbonate | 836.0 |
| Saccharin sodium | 11.0 |
| Polyvinylpyrrolidone | 40.0 |
| 10% w/w siliconed sodium benzoate | 80.0 |
| Lemon flavour powder | 25.0 |
| Pharmaceutical industrial alcohol for granulation | |

*Equivalent to 150 mg free base.

The ranitidine hydrochloride, anhydrous monosodium citrate, sodium bicarbonate and saccharin sodium were mixed together, and granulated by the addition of a solution of the polyvinylpyrrolidone in the alcohol. The granules obtained after mixing were dried and passed through a calibrator, and the resulting granules were then mixed with the sodium benzoate and lemon flavouring. The granulated material was compressed into tablets using an alternative machine fitted with 20 mm punches.

A rotative machine fitted with 20 mm punches may also be used for tabletting.

EXAMPLE 2

|  | mg/2 g tablet |
| --- | --- |
| Ranitidine hydrochloride | 168.0* |
| Anhydrous monosodium citrate | 840.0 |
| Sodium bicarbonate | 836.0 |
| Saccharin sodium | 11.0 |
| Polyvinylpyrrolidone | 40.0 |
| 10% w/w siliconed sodium benzoate | 80.0 |
| Orange flavour powder | 16.65 |
| Grapefruit flavour powder | 8.35 |
| Pharmaceutical industrial alcohol for granulation | |

*Equivalent to 150 mg free base.

The tablets were prepared as described in Example 1, but with the replacement of lemon flavour powder by orange and grapefruit flavouring.

EXAMPLE 3

|  | mg/3 g tablet |
| --- | --- |
| Ranitidine hydrochloride | 336.0* |
| Anhydrous monosodium citrate | 1236.7 |
| Sodium bicarbonate | 1230.8 |
| Saccharin sodium | 16.5 |
| Polyvinylpyrrolidone | 45.0 |
| 10% w/w siliconed sodium benzoate | 90.0 |
| Grapefruit flavour powder | 15.0 |
| Orange flavour powder | 30.0 |
| Pharmaceutical industrial alcohol for granulation | |

*Equivalent to 300 mg free base.

The ranitidine hydrochloride, anhydrous monosodium citrate, sodium bicarbonate and saccharin sodium were mixed together, and granulated by the addition of a solution of the polyvinylpyrrolidone in the alcohol. The granules obtained after mixing were dried and passed through a calibrator, and the resulting granules were then mixed with the sodium benzoate and orange and grapefruit flavouring. The granulated material was compressed into tablets using an alternative machine fitted with 23 mm punches.

EXAMPLE 4

|  | mg/3 g tablet |
| --- | --- |
| Ranitidine hydrochloride | 336.0* |
| Anhydrous monosodium citrate | 1229.0 |
| Sodium bicarbonate | 1223.0 |
| Saccharin sodium | 17.0 |
| Polyvinylpyrrolidone | 60.0 |
| 10% w/w siliconed sodium benzoate | 120.0 |
| Mint flavouring | 15.0 |
| Pharmaceutical industrial alcohol for granulation | |

*Equivalent to 300 mg free base.

The tablets were prepared as in Example 3, but with the use of mint flavouring instead of orange and grapefruit flavouring.

In the above Examples 1 to 4, an appropriate amount of sodium cyclamate (for example 50–150 mg, preferably 80 mg in a 150 mg unit dose and 120 mg in a 300 mg unit dose) or aspartame (for example 20–60 mg, preferably 30 mg, in a 150 mg unit dose; and 40–80 mg in a 300 mg unit dose) may replace sodium saccharin as the sweetener.

EXAMPLE 5

|  | mg/2 g tablet |
| --- | --- |
| Ranitidine hydrochloride | 168.0* |
| Anhydrous monosodium citrate | 845.5 |
| Sodium bicarbonate | 841.5 |
| Aspartame | 30.0 |
| Polyvinylpyrrolidone | 30.0 |
| 10% w/w siliconed sodium benzoate | 60.0 |
| Lemon flavour powder | 25.0 |
| Pharmaceutical industrial alcohol for granulation | |

*Equivalent to 150 mg free base.

The ranitidine hydrochloride, anhydrous monosodium citrate, sodium bicarbonate and aspartame were mixed together, and granulated by the addition of a solution of the polyvinylpyrrolidone in the alcohol. The granules obtained after mixing were dried and passed through a calibrator, and the resulting granules were then mixed with the sodium benzoate and lemon flavouring. The granulated material was compressed into tablets using an alternative machine fitted with 20 mm punches.

A rotative machine fitted with 20 mm punches may also be used for tabletting.

Examples 6 to 8 illustrate effervescent compositions according to the invention for a sachet presentation.

EXAMPLE 6

|  | % (w/w) |
| --- | --- |
| Ranitidine hydrochloride | 11.200 |
| Anhydrous monosodium citrate | 41.975 |
| Sodium bicarbonate | 41.775 |
| Saccharin sodium | 0.550 |
| Polyvinylpyrrolidone | 3.000 |
| Flavour powder | 1.500 |
| Pharmaceutical industrial alcohol for granulation. | |

The ingredients (apart from the flavour powder) were mixed and granulated, and the resulting granules passed through a calibrator, as described for the preparation of tablets in Examples 1 to 5 above. The granules obtained were mixed with the flavouring, and the resulting mix was filled into sachets, 1.5 g for a 150 mg. unit dose of ranitidine, and 3.0 g for a 300 mg. unit dose of ranitidine (unit doses expressed as the weight of free base).

The flavour powder may be lemon or a mixture of orange and grapefruit.

EXAMPLE 7

|  | mg/1.5 g portion |
| --- | --- |
| Ranitidine hydrochloride | 168.0* |
| Anhydrous monosodium citrate | 629.625 |
| Sodium bicarbonate | 626.625 |
| Saccharin sodium | 8.25 |
| Polyvinylpyrrolidone | 45.0 |
| Lemon flavour powder | 22.5 |
| Pharmaceutical industrial alcohol for granulation. | |

*Equivalent to 150 mg free base.

The ingredients (apart from the flavour powder) were mixed and granulated, and the resulting granules passed through a calibrator, as described for the preparation of tablets in Examples 1 to 5 above. The granules obtained were mixed with the lemon flavouring, and the resulting mix was filled into sachets in 1.5 g portions, giving a 150 mg. unit dose of ranitidine (expressed as the weight of free base).

If desired, the lemon flavouring may be replaced by an appropriate amount of a mixture of orange and grapefruit flavour powder.

EXAMPLE 8

|  | mg/3 g portion |
| --- | --- |
| Ranitidine hydrochloride | 336.0* |
| Anhydrous monosodium citrate | 1259.25 |
| Sodium bicarbonate | 1253.25 |
| Saccharin sodium | 16.5 |
| Polyvinylpyrrolidone | 90.0 |
| Grapefruit flavour powder | 15.0 |
| Orange flavour powder | 30.0 |
| Pharmaceutical industrial alcohol for granulation. | |

*Equivalent to 300 mg free base.

The ingredients (apart from the flavour powder) were mixed and granulated, and the resulting granules passed through a calibrator, as described for the preparation of tablets in Examples 1 to 5 above. The granules obtained were mixed with the orange and grapefruit flavouring, and the resulting mix was filled into sachets in 3.0 g portions, giving a 300 mg. unit dose of ranitidine (expressed as the weight of free base).

If desired, the orange and grapefruit flavouring may be replaced by an appropirate amount of lemon flavour powder.

In the above Examples 6 to 8, an appropriate amount of sodium cyclamate or aspartame may replace sodium saccharin as the sweetener (as described in connection with tablet Examples 1 to 4).

I claim:

1. An effervescent pharmaceutical composition for oral use in the treatment of a condition mediated through histamine $H_2$-receptors, the composition combining the required degree of stability with a rapid rate of dissolution, the composition comprising an effective amount of ranitidine or a physiologically acceptable salt thereof to relieve said condition, and effective amounts of an alkali metal citrate and an alkaline carbonate or bicarbonate to produce the effervescence, characterised in that the alkali metal citrate is solely a monoalkali metal citrate.

2. A pharmaceutical composition as claimed in claim 1 containing ranitidine hydrochloride.

3. A pharmaceutical composition as claimed in claim 1 wherein the monoalkali metal citrate is monosodium citrate.

4. A pharmaceutical composition as claimed in claim 1 wherein the alkaline carbonate or bicarbonate is an alkali metal or alkaline earth metal carbonate or bicarbonate.

5. A pharmaceutical composition as claimed in claim 4 wherein the alkaline carbonate or bicarbonate is sodium bicarbonate.

6. A pharmaceutical composition as claimed in claim 1 in unit dose form containing 50 to 600 mg. ranitidine per unit dose expressed as the weight of free base.

7. A pharmaceutical composition as claimed in claim 1 in unit dose form containing 50 to 500 mg. ranitidine per unit dose expressed as the weight of free base.

8. A pharmaceutical composition as claimed in claim 6 containing 150 to 300 mg. ranitidine per unit dose.

9. A pharmaceutical composition as claimed in claim 1 containing 25% to 55% (w/w) monoalkali metal citrate.

10. A pharmaceutical composition as claimed in claim 1 containing 25% to 55% (w/w) alkaline carbonate or bicarbonate.

11. An effervescent pharmaceutical composition for oral use in the treatment of a condition mediated through histamine $H_2$-receptors, the composition combining the required degree of stability with a rapid rate of dissolution, the composition comprising an effective amount of ranitidine hydrochloride to relieve said condition, and effective amounts of monosodium citrate and sodium bicarbonate to produce the effervescence, wherein the monosodium citrate is the only citrate present.

12. A pharmaceutical composition as claimed in claim 11 comprising ranitidine hydrochloride (2% to 30% w/w), monosodium citrate (35% to 45% w/w) and sodium bicarbonate (35% to 45% w/w).

13. A pharmaceutical composition as claimed in claim 12 in unit dose form containing 150 to 300 mg. ranitidine per unit dose, expressed as the weight of free base.

14. A pharmaceutical composition as claimed in claim 1 containing at least one physiologically acceptable carrier or excipient.

15. A pharmaceutical composition as claimed in claim 1 in the form of tablets, granules or a powder.

16. A pharmaceutical composition as claimed in claim 15 in the form of tablets.

17. A pharmaceutical composition as claimed in claim 16 containing a binding agent (1% to 2% w/w) and a lubricant (2% to 4% w/w).

18. A pharmaceutical composition as claimed in claim 15 in the form of sachets containing a fixed dose of powder or granules.

19. A pharmaceutical composition as claimed in claim 18 containing a binding agent (2% to 4% w/w).

20. A pharmaceutical composition as claimed in claim 1 additionally containing one or more flavouring and/or sweetening agents.

21. A pharmaceutical composition as claimed in claim 11 comprising ranitidine hydrochloride (2% to 30% w/w), monosodium citrate (35% to 45% w/w) and sodium bicarbonate (35% to 45% w/w), and additionally containing sodium saccharin as a sweetening agent, in which the ranitidine content is 150 mg per unit dose (expressed as the weight of free base).

22. A pharmaceutical composition as claimed in claim 11 comprising ranitidine hydrochloride (2% to 30% w/w), monosodium citrate (35% to 45% w/w) and sodium bicarbonate (35% to 45% w/w), and additionally containing sodium cyclamate as a sweetening agent, in which the ranitidine content is 150 mg per unit dose (expressed as the weight of free base).

23. A pharmaceutical composition as claimed in claim 11 comprising ranitidine hydrochloride (2% to 30% w/w), monosodium citrate (35% to 45% w/w) and sodium bicarbonate (35% to 45% w/w), and additionally containing aspartame as a sweetening agent, in which the ranitidine content is 150 mg per unit dose (expressed as the weight of free base).

24. A pharmaceutical composition as claimed in claim 11 comprising ranitidine hydrochloride (2% to 30% w/w), monosodium citrate (35% to 45% w/w) and sodium bicarbonate (35% to 45% w/w), and additionally containing sodium saccharin as a sweetening agent, in which the ranitidine content is 300 mg per unit dose (expressed as the weight of free base).

25. A pharmaceutical composition as claimed in claim 11 comprising ranitidine hydrochloride (2% to 30% w/w), monosodium citrate (35% to 45% w/w) and sodium bicarbonate (35% to 45% w/w), and additionally containing sodium cyclamate as a sweetening agent, in which the ranitidine content is 300 mg per unit dose (expressed as the weight of free base).

26. A pharmaceutical composition as claimed in claim 11 comprising ranitidine hydrochloride (2% to 30% w/w), monosodium citrate (35% to 45% w/w) and sodium bicarbonate (35% to 45% w/w), and additionally containing aspartame as a sweetening agent, in which the ranitidine content is 300 mg per unit dose (expressed as the weight of free base).

27. A pharmaceutical composition as claimed in claim 7 containing 150 to 300 mg. ranitidine per unit dose.

28. A pharmaceutical composition as claimed in claim 11 containing at least one physiologically acceptable carrier or excipient, said composition being in the form of tablets, granules or a powder.

29. A pharmaceutical composition as claimed in claim 28 in the form of tablets.

30. A pharmaceutical composition as claimed in claim 29 containing a binding agent (1% to 2% w/w) and a lubricant (2% to 4% w/w).

31. A pharmaceutical composition as claimed in claim 28 in the form of sachets containing a fixed dose of powder or granules.

32. A pharmaceutical composition as claimed in claim 31 containing a binding agent (2% to 4% w/w).

33. A pharmaceutical composition as claimed in claim 11 additionally containing one or more flavouring and-/or sweetening agents.

* * * * *

UNITED STATES PATENT AND TRADEMARK OFFICE
CERTIFICATE OF CORRECTION

PATENT NO. : 5,102,665
DATED : April 7, 1992
INVENTOR(S) : Alain Emile Edouard SCHAEFFER It is certified that error appears in the above-indentified patent and that said Letters Patent is hereby corrected as shown below:

On the title page, item [73] Assignee, please change "Glaxo Group Limited" to --Laboratories Glaxo S.A.--.

Signed and Sealed this

Nineteenth Day of July, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,102,665

DATED : April 7, 1992

INVENTOR(S) : Alain Emile Edouard SCHAEFFER

It is certified that error appears in the above-indentified patent and that said Letters Patent is hereby corrected as shown below:

On the title page, item [73] Assignee, please change "Laboratories Glaxo S.A." to --Laboratoires Glaxo S.A.--.

This certificate supersedes certificate of correction issued July 19, 1994.

Signed and Sealed this

First Day of August, 1995

Attest:

BRUCE LEHMAN

Attesting Officer    Commissioner of Patents and Trademarks